United States Patent
DiFoggio

(10) Patent No.: US 7,240,546 B2
(45) Date of Patent: Jul. 10, 2007

(54) METHOD AND APPARATUS FOR DOWNHOLE DETECTION OF CO2 AND H2S USING RESONATORS COATED WITH CO2 AND H2S SORBENTS

(76) Inventor: Rocco DiFoggio, 12006 Plumpoint Dr., Houston, TX (US) 77099

( * ) Notice: Subject to any disclaimer, the term of this patent is extended or adjusted under 35 U.S.C. 154(b) by 112 days.

(21) Appl. No.: 10/917,173

(22) Filed: Aug. 12, 2004

(65) Prior Publication Data

US 2006/0032301 A1 Feb. 16, 2006

(51) Int. Cl.
*E21B 49/08* (2006.01)
(52) U.S. Cl. ............................. 73/152.23; 73/152.54
(58) Field of Classification Search ............ 73/152.25, 73/152.54, 152.23
See application file for complete search history.

(56) References Cited

U.S. PATENT DOCUMENTS

| | | | | |
|---|---|---|---|---|
| 2,814,947 A | * | 12/1957 | Stegemeier et al. | 73/152.18 |
| 3,329,004 A | * | 7/1967 | King, Jr. | 73/24.06 |
| 4,154,660 A | * | 5/1979 | Micko | 205/786.5 |
| 4,905,701 A | * | 3/1990 | Cornelius | 600/437 |
| 5,179,028 A | * | 1/1993 | Vali et al. | 436/524 |
| 5,351,532 A | * | 10/1994 | Hager | 73/152.55 |
| 5,734,098 A | * | 3/1998 | Kraus et al. | 73/61.62 |
| 5,783,747 A | * | 7/1998 | Lindow et al. | 73/61.41 |
| 5,829,520 A | * | 11/1998 | Johnson | 166/250.01 |
| 6,101,871 A | * | 8/2000 | Schultz | 73/152.25 |
| 6,272,938 B1 | * | 8/2001 | Baghel et al. | 73/863.23 |
| 6,336,353 B2 | * | 1/2002 | Matsiev et al. | 73/24.06 |
| 6,938,470 B2 | * | 9/2005 | DiFoggio et al. | 73/152.24 |
| 2002/0194906 A1 | | 12/2002 | Goodwin et al. | |
| 2003/0033866 A1 | * | 2/2003 | Diakonov et al. | 73/152.55 |
| 2004/0045350 A1 | * | 3/2004 | Jones et al. | 73/152.23 |
| 2004/0159149 A1 | * | 8/2004 | Williams et al. | 73/152.23 |
| 2004/0173017 A1 | | 9/2004 | O'Brien | |
| 2005/0000279 A1 | * | 1/2005 | Yogeswaren | 73/152.58 |
| 2005/0086998 A1 | * | 4/2005 | Qin | 73/31.07 |
| 2005/0109098 A1 | * | 5/2005 | DiFoggio | 73/152.55 |
| 2005/0120813 A1 | * | 6/2005 | Clark et al. | 73/866.5 |
| 2005/0241382 A1 | * | 11/2005 | Coenen | 73/152.19 |

* cited by examiner

*Primary Examiner*—Hezron Williams
*Assistant Examiner*—John Fitzgerald
(74) *Attorney, Agent, or Firm*—Madan, Mossman & Sriram, P.C.

(57) ABSTRACT

A formation fluid sample is exposed to a rigidly-supported semi-permeable membrane such as silicone rubber to permit diffusion of gases and vapors from the formation fluid into a vacuum chamber, while at the same time, blocking the passage of any liquids. The membrane-transmitted gas is analyzed in the vacuum chamber by a resonator that reacts with it. The resulting change in resonant frequency of the resonator indicates the presence of a gas that reacts with it. An ion pump or sorbent is associated with the evacuated chamber to maintain the vacuum. The ion pump or sorbent removes gases and vapors from the low-pressure chamber, which have diffused into it from the reservoir sample that is on the opposite (high-pressure) side of the semi-permeable membrane.

44 Claims, 7 Drawing Sheets

Gas Permeabilities $10^{-9}$ cc gas (RTP) cmsec $cm^2$cm Hg DP

| GAS | SSP-M100 | GAS | SSP-M100 |
|---|---|---|---|
| $H_2$ | 55 | n-$C_{10}H_{22}$ | 360 |
| He | 30 | HCHO | 925 |
| $NH_3$ | 500 | $CH_3OH$ | 1160 |
| $H_2O$ | 3000 | $COCL_2$ | 1250 |
| CO | 30 | Acetone | 490 |
| $N_2$ | 25 | Pyridine | 1595 |
| NO | 50 | Benzene | 900 |
| $O_2$ | 50 | Phenol | 1750 |
| $H_2S$ | 840 | Toluene | 760 |
| Ar | 50 | Xe | 171 |
| $CO_2$ | 270 | $CCl_4$ | 5835 |
| $N_2O$ | 365 | $CH_2O$ | 925 |
| $NO_2$ | 635 | Freon 11 | 1290 |
| $SO_2$ | 1250 | Freon 12 | 107 |
| $CS_2$ | 7500 | Freon 22 | 382 |
| $CH_4$ | 80 | Freon 114 | 211 |
| $C_2H_6$ | 210 | Freon 115 | 51 |
| $C_2H_4$ | 115 | | |
| $C_2H_2$ | 2200 | | |
| $C_3H_8$ | 340 | GAS | SSP-M213** |
| n-$C_4H_{10}$ | 750 | $CO_2$ | 97 |
| n-$C_5H_{12}$ | 1670 | $H_2$ | 21 |
| n-$C_6H_{14}$ | 785 | $O_2$ | 16 |
| n-$C_8H_{18}$ | 715 | $N_2$ | 7 |

*FIG. 6*

METHOD AND APPARATUS FOR DOWNHOLE DETECTION OF CO2 AND H2S USING RESONATORS COATED WITH CO2 AND H2S SORBENTS

BACKGROUND OF THE INVENTION

1. Field of the Invention

The present invention relates generally to downhole reservoir characterization and in particular to a method and apparatus for real time identification of CO2 and H2S gases diffused out of a formation fluid sample. Formation fluid samples are obtained and gases are allowed to diffuse from these fluid samples through a silicone rubber layer backed by a sintered metal filter and perforated backing plate acting as semi-permeable membrane into an evacuated chamber. The gases are analyzed in the evacuated chamber by a resonator coated with a CO2 or H2S sorbent and a processor, which identifies gases such as CO2 and H2S and other gases or vapors extracted from a downhole reservoir fluid or sample.

2. Summary of the Related Art

To obtain hydrocarbons such as oil and gas, boreholes are drilled into the earth by rotating a drill bit attached at to the end of a drill string. Modern directional drilling systems generally employ a drill string having a bottom hole assembly (BHA) and a drill bit at an end thereof that is rotated by a drill motor (mud motor) and/or by rotating the drill string. A number of downhole devices placed in close proximity to the drill bit measure certain downhole operating parameters associated with the drill string. Such devices typically include sensors for measuring downhole temperature and pressure, azimuth and inclination measuring devices and a resistivity-measuring device to determine the presence of hydrocarbons and water. Additional downhole instruments, known as logging-while-drilling (LWD) tools, are frequently attached to the drill string to determine the formation geology and formation fluid conditions during the drilling operations.

Commercial development of hydrocarbon fields requires significant amounts of capital. Before field development begins, operators desire to have as much data as possible regarding the nature of the hydrocarbon formation, in order to evaluate the reservoir for commercial viability. Despite the advances in data acquisition during drilling using the MWD systems and wireline analysis applications, it is often desirable to conduct further testing of the hydrocarbon reservoirs in order to obtain additional data. Therefore, after the well has been drilled, the hydrocarbon zones are often tested with other test equipment such as wireline tools, which are used to further analyze and monitor the formation.

One type of post-drilling test involves producing fluid from the reservoir and collecting such fluid samples downhole in tanks for transport to surface laboratories where Pressure-Volume-Temperature (PVT) studies and fluid properties such as density, viscosity and composition are measured. Also, one can measure the downhole fluid pressure at several depths and, from this pressure gradient, calculate the fluid's density.

Fluid samples extracted downhole are typically analyzed weeks to months later in a surface laboratory to identify and quantify gases present in the fluid. It is time consuming to retrieve fluid samples downhole and send them to a surface lab for analysis of gas content. Moreover, surface analysis requires removal of the fluid sample and the tool from the borehole for testing the sample before additional exploration and/or production activities occur. Thus, there is a need for a real-time downhole method and apparatus for detection, distinction and quantification of gases in the formation.

SUMMARY OF THE INVENTION

The present invention provides a method and apparatus for real-time downhole detection, distinction and quantification of gases such as CO2 and H2S and other gases and vapors present in a formation fluid sample. The present invention exposes downhole high-temperature and high-pressure formation fluids to a silicone rubber filter backed by a sintered metal filter backed by a perforated metal plate, forming semi-permeable membrane, which blocks liquids but allows passage of certain gases and vapors. This membrane is mechanically supported by a rigid but porous and permeable structure such as a perforated metal plate. The perforated metal plate is capable of withstanding the pressure difference between vacuum and downhole pressures. The semi-permeable membrane is made of a material such as silicone rubber, which permits the diffusion of gases and certain vapors from the formation fluid sample, through the membrane and into a vacuum chamber adjacent the semi-permeable membrane.

The vacuum chamber forms a gas analysis chamber containing a resonator coated with a CO2 or H2S sorbent. A formation fluid sample is captured in a downhole tool and filtered by a semi-permeable membrane such as silicone rubber to permit diffusion of gases from the formation fluid into a vacuum chamber. The gases diffuse out of the formation fluid and analyzed by sorbent coated resonator situated in the evacuated portion of a gas analysis chamber.

An ion pump is associated with the evacuated gas analysis chamber to maintain a vacuum in the chamber. The ion pump removes gases, which have diffused from the formation fluid sample into the evacuated chamber on the opposite side of the semi-permeable membrane filter. The ion pump can be turned off during the time that a gas concentration measurement is being made by the resonator. Alternatively, the ion pump can be left on but either physically positioned so as to restrict its pumping ability or electronically controlled so as to pump slow enough that the resonator has an opportunity to sense the gas before the pump has brought the vacuum back to its baseline value. In place of an ion pump, activated charcoal or some other sorbent could be used to prevent the gases that have diffused into the vacuum from lingering there too long and interfering with the measurement of subsequent gases that have evolved from the next sample.

BRIEF DESCRIPTION OF THE FIGURES

The novel features of this invention, as well as the invention itself, will be best understood from the attached drawings, taken along with the following description, in which similar reference characters refer to similar parts, and in which:

FIG. 6 is a table showing some examples of gas diffusion rates through a suitable semi-permeable membrane for use with the present invention.

DESCRIPTION OF AN EXEMPLARY EMBODIMENT

The present invention provides a method and apparatus for real-time downhole detection, classification and quantification of gases present in a representative formation fluid sample. Gases such as H2S and CO2 other gases and vapors present in a formation fluid sample are quantified by the present invention. The present invention exposes downhole high-temperature high-pressure formation fluid to a semi-permeable membrane such as silicone rubber to permit diffusion of gases from the formation fluid sample into a vacuum chamber containing a sorbent coated resonator.

The present invention analyzes high-temperature, high-pressure reservoir fluids by extracting and submitting a gaseous fraction of a formation fluid or fluid sample to a sorbent coated resonator. A formation fluid sample is acquired or captured and filtered through a semi-permeable membrane, such as silicone rubber to permit diffusion of gases from the formation fluid sample past the filter into a gas analysis chamber. In the present example of the invention the gas analysis chamber is evacuated to facilitate diffusion of gases from the formation or wellbore fluid into an evacuated gas analysis chamber. The diffused gas is analyzed by a sorbent coated resonator situated in the evacuated gas analysis chamber opposite the formation fluid chamber on the other side of the semi-permeable membrane. In the present example of the invention, an ion pump is associated with the evacuated gas analysis chamber to help establish and to maintain a vacuum in the chamber and to facilitate diffusion of gases from the fluid to the gas analysis chamber by maintaining a lower concentration of gas on the vacuum side of the membrane than there is in the fluid on the high pressure side of the membrane. Diffusion of a gas through a membrane is proportional to the concentration gradient of that gas across the membrane. The ion pump removes gases from the evacuated chamber, which have diffused into the evacuated chamber from the formation fluid sample located on the opposite side of the semi-permeable membrane filter.

The first function is to evacuate a vacuum chamber containing a resonator and processor to analyze gases. The vacuum chamber also is provided with an ion pump to maintain the vacuum. A semi-permeable membrane (such as silicone rubber) is placed at the inlet to the vacuum chamber to allow gases to diffuse into the vacuum chamber, while at the same time preventing liquids from entering the evacuated chamber.

Figure 1:
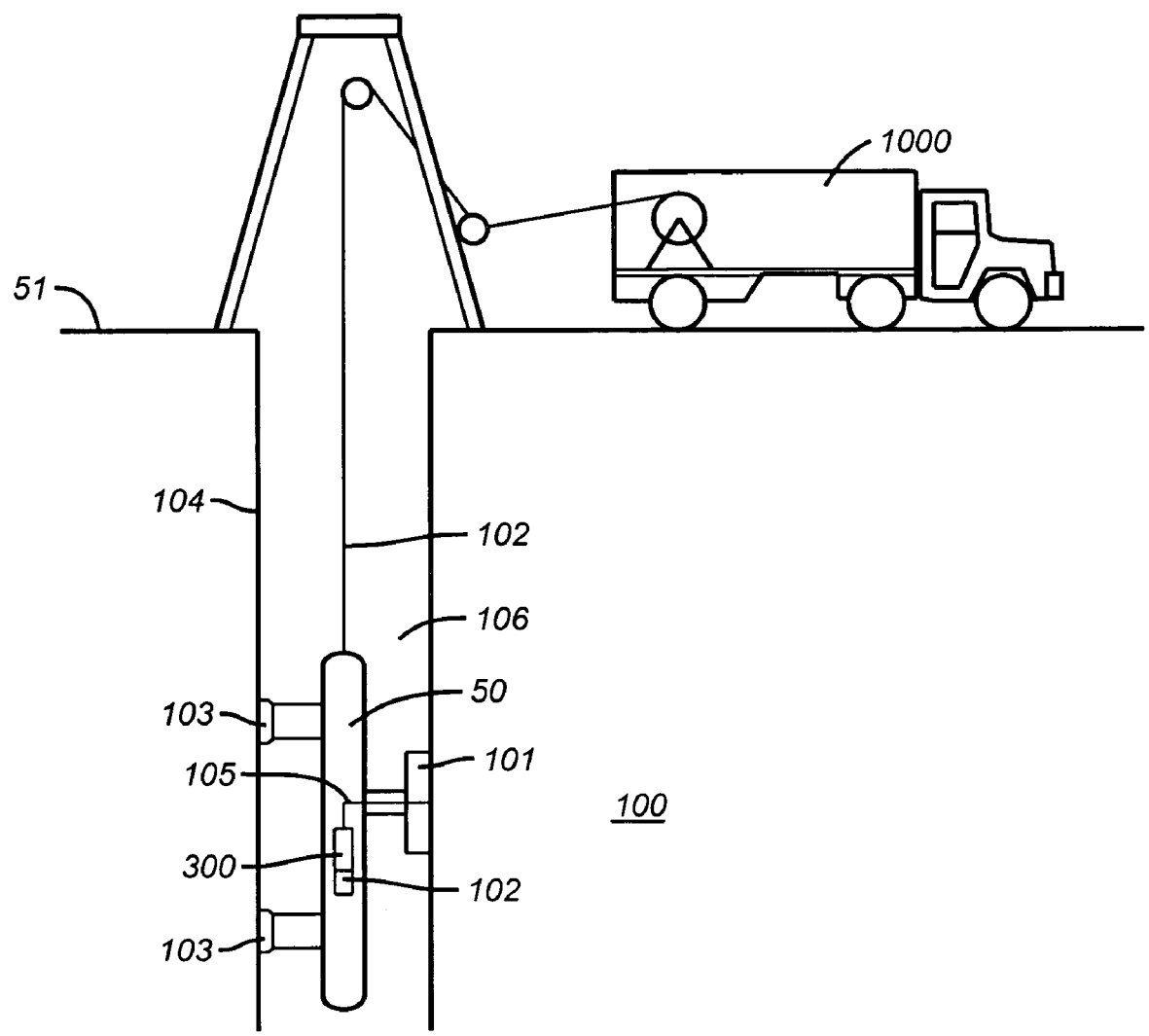
FIG. 1 is an illustration of an exemplary embodiment of the present invention as deployed in a borehole from a wireline.

Turning now to FIG. 1, FIG. 1 illustrates an example of the current invention deployed from a wireline 102 in a borehole 104 drilled in a formation 100. An extensible probe 101 extracts fluid from the formation 100. The extracted formation fluid flow through flow line 105 where the gas analysis chamber 300 of the present invention determines the gas content of the formation fluid sample. Stablizers 103 hold the tool 50 and extensible probe 101 in place during extraction of a formation fluid sample. The results of the gas analysis performed by a resonator 317 in gas analysis chamber 300 and processor 102, can be acted on by processor 102 or the analysis results can be sent to the surface 51 to acted on by the surface processor and control unit 1000. A well bore fluid can also be analyzed by extracting fluid from the well bore instead of the formation.

Figure 2:
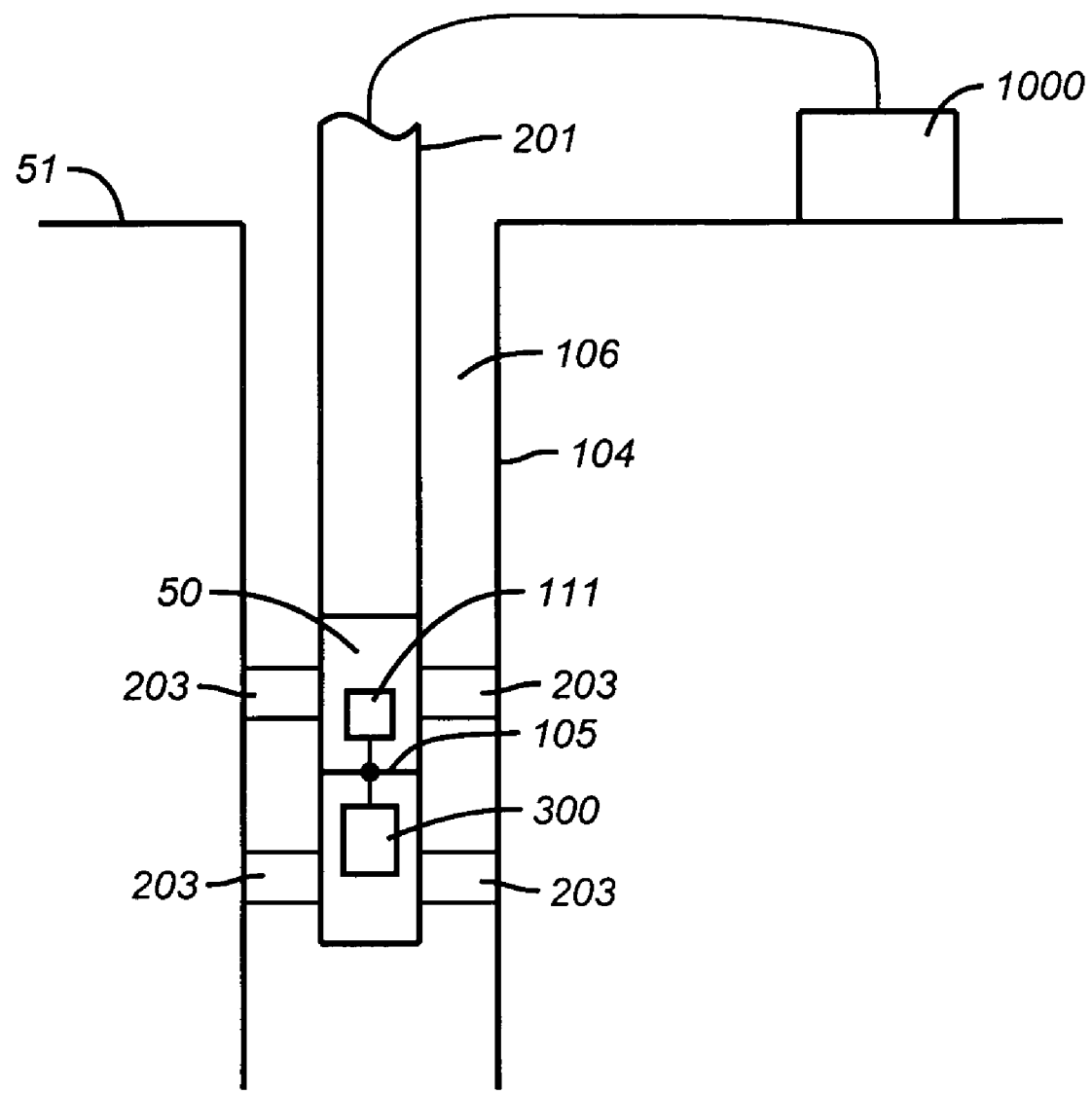
FIG. 2 is an illustration of an exemplary embodiment of the present invention as deployed in a borehole from a drill string.

Turning now to FIG. 2, another example of the current invention is shown deployed from a drill string 201. Straddle packers 203 hold the tool 50 in place during the entry of fluid through flow path 105 to the gas analysis chamber 300 of the present invention. The fluid can come from the annulus 105 between the tool 50 and the well bore 104 or from the formation 100. Fluid can be routed to the sample tank 111 or back to the well bore annulus 105 as desired based on the results of the density determination performed in the gas analysis chamber 300 of the present invention. The results of the gas analysis chamber are acted on by the processor 102, or the results can be sent to the surface 51 to acted on by surface processor and control 1000. A well bore fluid can also be analyzed by extracting fluid from the well bore instead of the formation.

Figure 3:
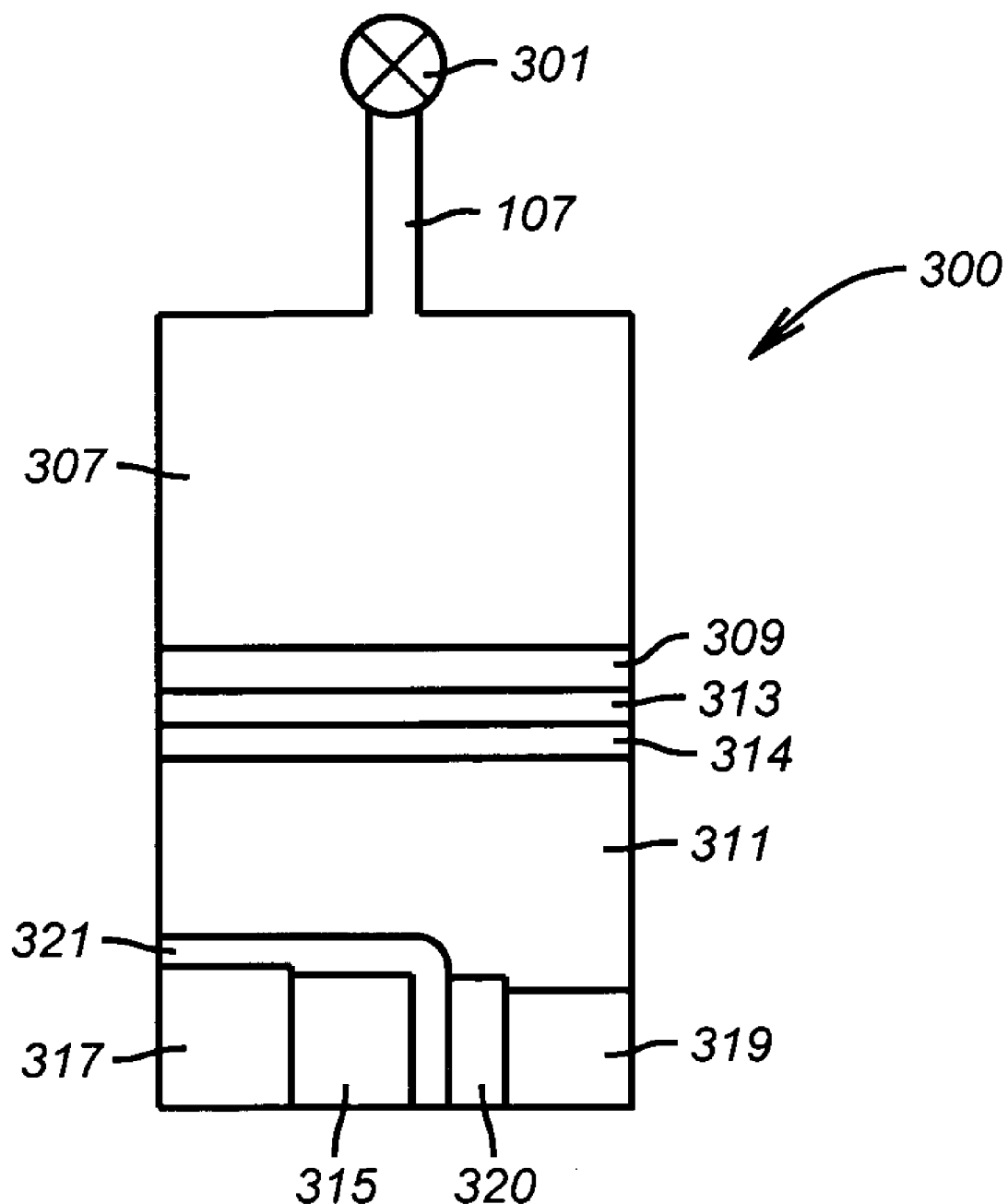
FIG. 3 is an illustration of the components comprising the current example of the invention.

Turning now to FIG. 3, a more detailed schematic of the gas analysis chamber 300 of the present invention is shown. A sorbent coated resonator 317, ion pump 319, semi-permeable membrane 309, fluid containment chamber 307 and processor 315 are shown in schematic form in FIG. 3. A sorption-cooling unit 321 is provided to maintain processor and resonator control electronics within their operating and/or survival temperature range. The formation fluid containment chamber 307 is separated from the evacuated gas analysis chamber 311 by the semi-permeable membrane 309. Thus, the formation fluid containment chamber 307 is positioned on one side of the semi-permeable membrane 309 and an evacuated gas analysis chamber 311 on the other side of the semi-permeable membrane 309. The gases present in the formation fluid sample diffuse across the semi-permeable membrane into the evacuated gas analysis chamber for analysis. Activated charcoal or other gas sorbent 320 is placed in the gas analysis chamber to adsorb gases to prevent them from lingering in the gas analysis chamber too long.

Figure 4:
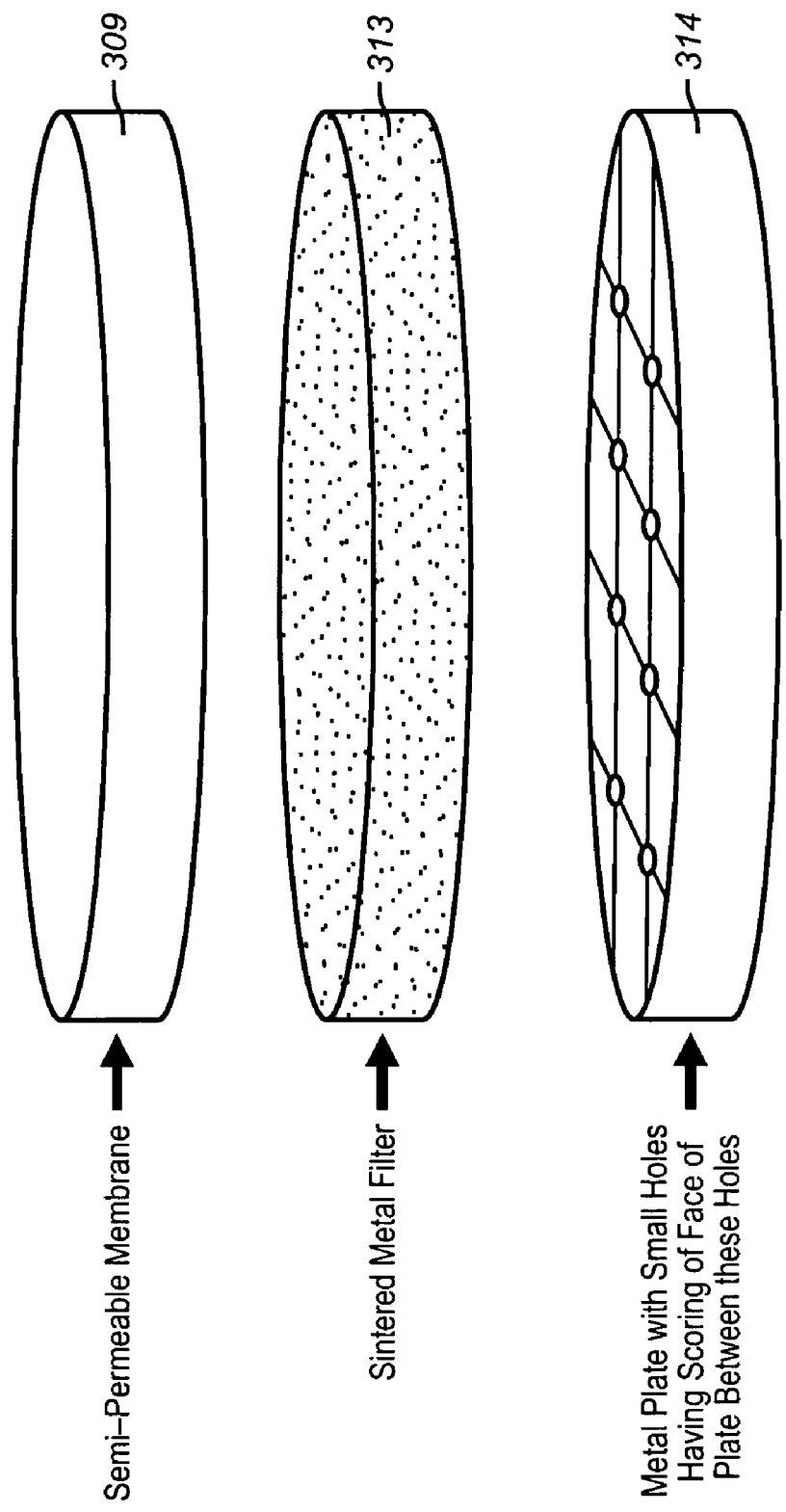
FIG. 4 illustrates the semi-permeable membrane, sintered metal filter and metal plate with small hole having scoring of fact of plate between the holes.

Formation fluid is extracted from the formation 100 or the well bore when the probe is not in contact with the well bore wall and enters into the fluid containment chamber 307 via flow line 107 and valve 301. Gases diffuse from the formation fluid or well bore fluid on the fluid side of the semi-permeable membrane, through the semi-permeable membrane and into the evacuated chamber 311. The gas analysis module equipment, resonator 317 and processor/control electronics 315 are located in the evacuated gas analysis chamber 311. The gas is exposed to and analyzed by the resonator 317 and processor 102. The processor 102 and resonator electronics control and conduct the analysis. The processor 102 reports the analytical results to the surface via the wireline or other means of downhole communication. The processor 102 can act on the analysis results without reporting the results to the surface. FIG. 4 illustrates the semi-permeable membrane 309, sintered metal filter 313 and metal plate 314 with small hole having scoring of fact of plate between the holes.

Figure 5:
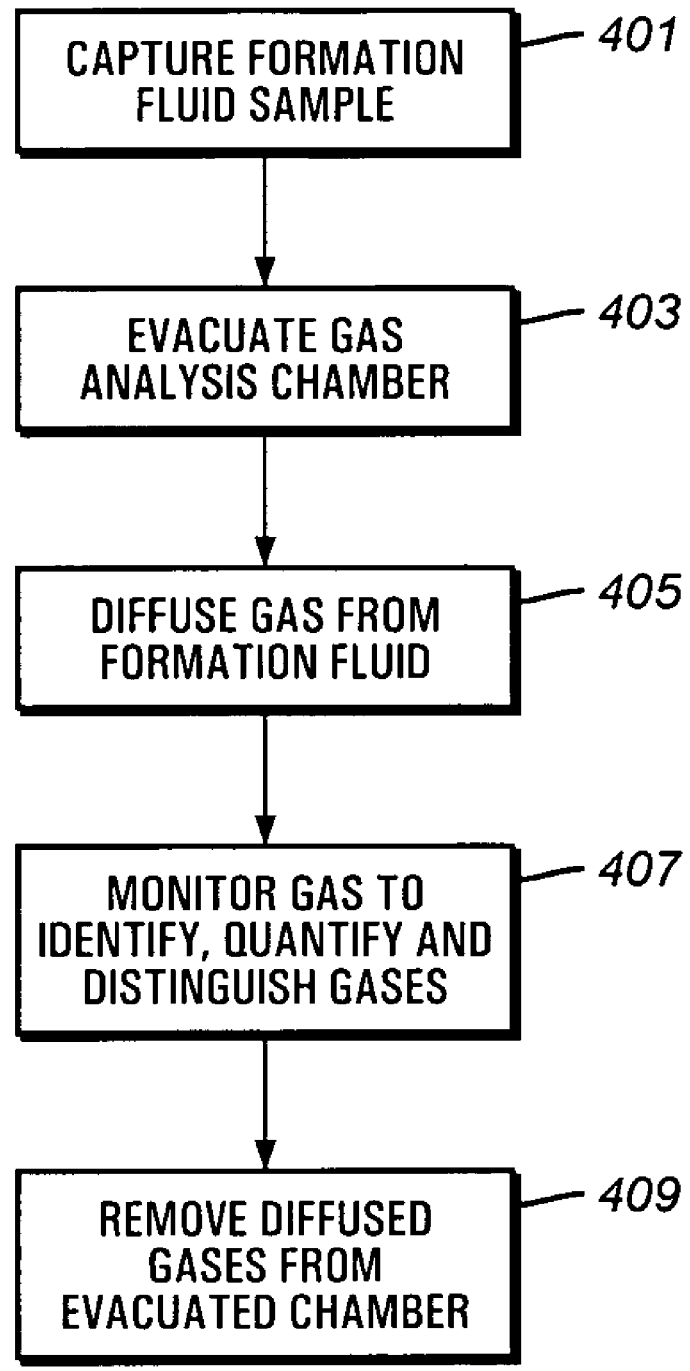
FIG. 5 is a flow chart of functions performed in an example of the present invention.

Turning now to FIG. 5, some of the functions performed by the present invention are illustrated. As shown in block 401, the present invention captures a formation fluid sample from the formation. The formation fluid enters the tool 50 via a flow line in fluid communication with the formation. In block 403, the gas analysis chamber is evacuated. The evacuation of the gas analysis chamber enables gases present in the formation fluid sample to diffuse from the fluid as gas into the evacuated chamber through the semi-permeable membrane. In block 405 the semi-permeable membrane between the fluid and the evacuated chamber allows gases from the fluid to diffuse through the semi-permeable membrane into an evacuated gas analysis chamber. In block 407, the resonator and processor of the present invention monitors the gases to detect, identify and quantify the gases and distinguish between them. In block 409, the ion pump removes excess or residual diffused gases from the evacuated side of the chamber to maintain the vacuum in preparation for the next measurement.

Sensors for CO2 and H2S are usually meant to operate in air or in vacuum. It is difficult to detect these gases while they are dissolved in crude oil. Thus a silicone rubber layer or other polymeric separation membrane, followed by a sintered stainless steel filter and a steel plant with a few holes in it covering a vacuum chamber are provided to separate gas and fluid. Thus, the gases can diffuse out of the crude oil and into a vacuum chamber containing the resonator. The chamber also contains activated charcoal 320 or other sorbent to prevent the gases from lingering too long in the chamber. When mass from diffused gas is deposited on the resonator, such as a tuning fork as used in the present example of the invention, the resonant frequency for the resonator is lowered. Thus, by coating a resonator with a material that selectively reacts with a particular gas, the presence of the particular gas can be detected by monitoring the resonate frequency of the resonator. In one embodiment the resonator is coated with silver, which reacts with H2S to produce black silver sulfide or tarnish and makes the resonator heavier, thus lowering it resonant frequency. In this case, a drop in the silver-coated resonator resonant frequency would indicate the presence of H2S. In another embodiment, the resonator is coated with copper or zinc or some other H2S reactive metal. In another embodiment, a resonator is coated with a sodium oxide to produce Na2CO3 when exposed to CO2, thus making the resonator heavier. In this case a reduction in the resonator resonant frequency would indicate the presence of CO2. A coating of tetramethylammonium fluoride tetrahydrate (TMAF) is useful for the detection of CO2 although TMAF also has some sensitivity to H2S.

Suitable semi-permeable membranes, activated charcoal sorbents and ion pumps are commercially available suitable for use with the present invention are discussed herein. Furthermore, membranes can be specially designed to be selective to the transmission of one gas instead of transmitting many gases as silicone membranes do. The invention enables diffusion and separation of CO2 and H2S from crude oil at high pressure and temperature and letting this gas diffuse through a semi-permeable membrane filter. In the high pressures of the downhole environment, membranes should be supported, thus, the present invention provides a sintered stainless steel filter analogous to sandstone with the sand particles replaced with steel particles. The sintered metal filter is porous and permeable. The sintered metal filter is backed by a perforated steel plate for rigid stability against the pressure of the fluid from which gases diffuse.

Separation membrane technology is discussed by Sandra Young of the School of Polymers at The University of Southern Mississippi, (see, e.g., http://www.psrc.usm.edu/mauritz/diffuse.html), which states:

Aromatic polyimides that contain —C(CF3)2— groups tend to have higher preference for CO2 relative to CH4. Introduction of —C(CF3)2— groups is believed to increase chain stiffness which reduces intrasegmental mobility, and reduce and limit the degree of chain packing by increasing the free volume, serving as molecular spacers and chain stiffeners in the polymer (Stern, S. A. J. Membrane Sci., 1994, 94, 1-65 and Kim, T. H.; Koros, W. J.; Husk, G. R.; O'Brien, K. C. J. Membrane Sci., 1988,37, 45-62).

Polysulfones have been used for years as perm-selective membranes, starting in 1977 when Monsanto utilized asymmetric hollow fiber coated with a thin layer of silicone rubber for H2 separations. Asymmetric cellulose acetate membranes are used for the removal of CO2 and H2S from natural gas. CO2 and H2S have high solubility in cellulose acetate, which induces pseudo-plasticization, causing the polymer to swell with disruption of the polymer matrix, which increases the mobility of the polymer chains. In the area of rubbery polymers, the only systems currently under investigation are the poly(organosiloxanes). Poly(organosiloxanes) have been studied in detail because of the vast utility of polydimethylsiloxane (PDMS) as a preformed membrane that can then be used as a template for IPN formation in gas or liquid separation processes. PDMS possesses one of the greatest permeability coefficients of any polymer, due to its large free volume, and low selectivity. Through copolymerization, properties have the potential to be tailored to suit specific separation needs. Porosity control in materials used for separation processes is essential due to the potential variability of gases or liquids through the membrane. Sol-gel polymerizations can be manipulated to adjust the shrinkage of a network for the development of controlled porosity inorganic materials.

John J. Pellegrino of National Institute of Standards and Technology states: http://membranes.nist.gov/publication-_abstracts/Pell_Ko_Nass_Eine.html CO2 and H2S can be selectively separated from each other and from non-polar gases, such as H2, CO and CH4 using chemically reactive carriers immobilized in a membrane phase. Ion-exchange membranes made from polyperfluorosulfonic acid (PFSA) have been modified to form a gel for use as the support for the solvent and carrier. The membrane contains hydrophilic regions into which a solvent, containing the desired chemical complexing agent, may be imbibed. In experiments performed at ambient conditions selectivities for CO2 versus H2 are 20 to 30 with CO2 permeabilities of 1000-2000 barrer. [1 barrer=$10^{-10}$ $cm^2 \cdot s^{-1} \cdot cmHg^{-1}$] Higher selectivities and H2S permeabilities are obtained for the H2S-H2 separation. Our studies include characterization of this membrane with a variety of amine carriers and polar solvents at ambient temperatures and pressure. This paper presents a summary of the acid gas permeation rates and selectivities for the acid gases versus H2 and CO. Preliminary economic evaluations indicate that composite membranes with PFSA coated films 5 to 1 μm thick, would have capital costs lower than standard amine-absorber technology.

Figure 7:
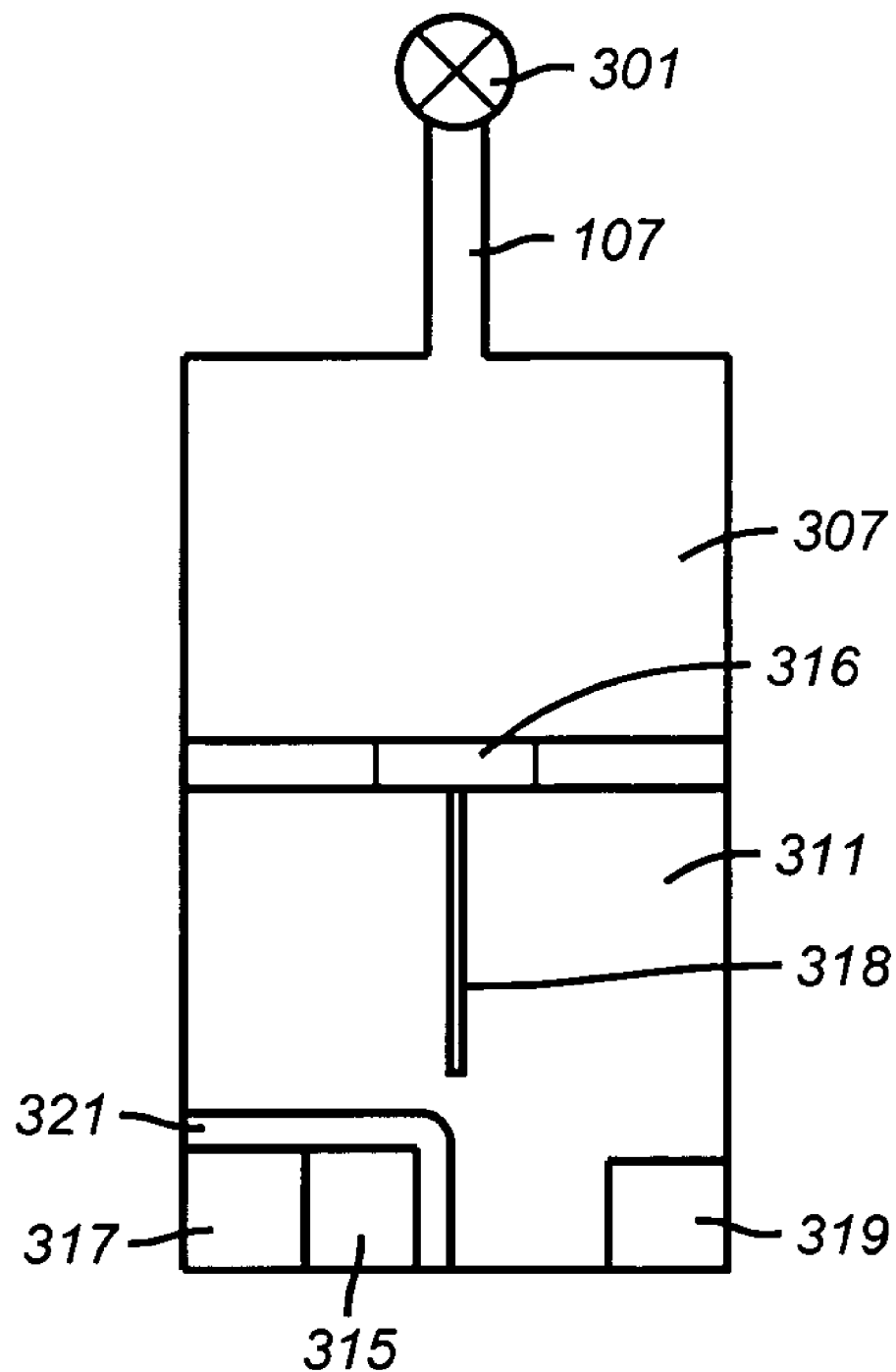
FIG. 7 illustrates an alternative embodiment having a filter and capillary tube input.

FIG. 6 is a tabular listing and specification for some gases through a representative semi-permeable membrane, which is suitable for use with the present invention. The specifications for some small commercially available resonators and small ion pumps are discussed below. FIG. 7 illustrates an alternative embodiment having a filter 316 and capillary tube 318 input to evacuated gas analysis chamber 311. There is typically a tradeoff between the speed of response to gases in a fluid and the thickness of the semi-permeable membrane.

In another embodiment of the present invention, the method of the present invention is implemented as a set computer executable of instructions on a computer readable medium, comprising ROM, RAM, CD ROM, Flash or any other computer readable medium, now known or unknown that when executed cause a computer to implement the method of the present invention.

While the foregoing disclosure is directed to the preferred embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated.

What is claimed is:

1. A method for monitoring the presence of a particular gas in a fluid downhole comprising:
   diffusing the particular gas from the fluid downhole into a gas analysis chamber by evacuating the gas analysis chamber;
   exposing the particular gas to a resonator that adsorbs the particular gas;
   monitoring a resonant frequency of the resonator to detect a change in the resonant frequency after being exposed to the gas; and
   estimating the presence of the particular gas in the fluid downhole based on the change in the resonant frequency.

2. The method of claim 1, further comprising:
   coating the resonator with a sorbent that adsorbs the particular gas.

3. The method of claim 2, wherein the particular gas is CO2.

4. The method of claim 2, wherein the particular gas is H2S.

5. The method of claim 1 wherein:
   the gas is diffused through a semi-permeable membrane.

6. The method of claim 5, further comprising: backing the semi-permeable membrane with a sintered metal.

7. The method of claim 5 further comprising:
   backing the semi-permeable membrane with a perforated backing plate.

8. The method of claim 5, wherein the semipermeable membrane comprises a gas selectable semi permeable membrane.

9. The method of claim 1, further comprising:
   removing at least one gas from the gas analysis chamber.

10. The method of claim 9, wherein removing is performed by:
    pumping the at least one gas from the gas analysis chamber.

11. An apparatus for monitoring the presence of a particular gas in a fluid downhole comprising:
    a membrane diffusing the particular gas from the fluid downhole into a gas analysis chamber;
    a resonator within the gas chamber;
    a processor for monitoring a resonant frequency of the resonator to detect a change in the resonant frequency after being exposed to the particular gas and estimating the presence of the particular gas in the fluid downhole based on the change in the resonant frequency; and
    a pump evacuating the gas analysis chamber to facilitate diffusion of the gas into the gas analysis chamber.

12. The apparatus of claim 11, further comprising:
    charcoal in the gas analysis chamber for adsorbing gases from the gas analysis chamber to prevent the gases from lingering in the gas analysis chamber.

13. The apparatus of claim 11, further comprising:
    an ion pump for pumping gases from the gas analysis chamber to prevent the gases from lingering in the gas analysis chamber.

14. The apparatus of claim 11, wherein the resonator further comprises:
    a sorbent that adsorbs the particular gas wherein the processor monitors the resonant frequency of the coated resonator to detect the presence of the particular gas in the fluid downhole.

15. The apparatus of claim 14, wherein the resonator further comprises:
    a CO2 sorbent for coating the resonator to detect the presence of CO2.

16. The apparatus of claim 14, wherein the resonator further comprises:
    a H2S sorbent tat coats the resonator to detect the presence of H2S.

17. The apparatus of claim 11 wherein the membrane is semi-permeable.

18. The apparatus of claim 17, wherein the membrane further comprises:
    a sintered metal backing the semi-permeable membrane.

19. The apparatus of claim 17 wherein the membrane further comprises:
    a perforated backing plate backing the semi-permeable membrane.

20. The apparatus of claim 17, wherein the membrane only allows only one or more gases to diffuse from the fluid downhole.

21. A system for monitoring the presence of a gas in a fluid downhole comprising:
    a downhole tool;
    a membrane for diffusing the gas from the fluid downhole into a gas analysis chamber in the downhole tool;
    a resonator for detecting the presence of the gas in the fluid downhole;
    a processor for monitoring a resonant frequency of the resonator to detect a change in the resonant frequency after being exposed to the gas and detecting the presence of the gas based on the change in the resonant frequency; and
    a pump evacuating the gas analysis chamber to facilitate diffusion of the gas into the gas analysis chamber.

22. The system of claim 21, wherein the membrane comprises a semipermeable membrane.

23. The system of claim 21, wherein the membrane comprises a gas selective membrane.

24. The system of claim 21, wherein the resonator is coated with a sorbent to detect the presence of the gas.

25. A method for monitoring the presence of a particular gas in a fluid downhole comprising:
    (a) diffusing the particular gas from the fluid downhole into a gas analysis chamber by establishing a vacuum in the gas analysis chamber to facilitate diffusion of the particular gas into the gas analysis chamber;
    (b) exposing the particular gas to a resonator that adsorbs the particular gas;
    (c) monitoring a resonant frequency of the resonator to detect a change in the resonant frequency after being exposed to the gas; and
    (d) estimating the presence of the particular gas in the fluid downhole based on the change in the resonant frequency.

26. The method of claim 25 further comprising:
    diffusing the gas through one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

27. The method of claim 25, wherein the particular gas is one of (i) CO2, and (ii) H2S.

28. The method of claim 25, further comprising:
removing at least one gas from the gas analysis chamber.

29. A method for monitoring the presence of a particular gas in a fluid downhole comprising:
(a) diffusin the particular gas from the fluid downhole into a gas analysis chamber through a membrane that is supported to withstand a pressure difference between a vacuum pressure in the chamber and a downhole pressure;
(b) exposing the particular gas to a resonator that adsorbs the particular gas;
(c) monitoring a resonant frequency of the resonator to detect a change in the resonant frequency after being exposed to the gas; and
(d) estimating the presence of the particular gas in the fluid downhole based on the change in the resonant frequency.

30. The method of claim 29 wherein the membrane is one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

31. The method of claim 29, wherein the particular gas is one of (i) CO2, and (ii) H2S.

32. The method of claim 29, further comprising:
removing at least one gas from the gas analysis chamber.

33. An apparatus for monitoring the presence of a particular gas in a fluid downhole comprising:
(a) a membrane diffusing the particular gas from the fluid downhole into a gas analysis chamber, wherein the gas analysis chamber forms a vacuum chamber;
(b) a resonator within the gas chamber; and
(c) a processor for monitoring a resonant frequency of the resonator to detect a change in the resonant frequency after being exposed to the particular gas and estimating the presence of the particular gas in the fluid downhole based on the change in the resonant frequency.

34. The apparatus of claim 33 wherein the membrane is one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

35. The apparatus of claim 33, wherein the resonator further comprises a sorbent for coating the resonator to detect the presence of one of: (i) C2, and (ii) H2S.

36. The apparatus of claim 33, further comprising charcoal in the gas analysis chamber for adsorbing gases from the gas analysis chamber to prevent the gases from lingering in the gas analysis chamber.

37. An apparatus for monitoring the presence of a particular gas in a fluid downhole;
(a) a membrane diffusing the particular gas from the fluid downhole into a gas analysis chamber, wherein the membrane is supported to withstand a pressure difference between a vacuum pressure in the chamber and a downhole pressure;
(b) a resonator within the gas chamber; and
(C) a processor for monitoring a resonant frequency of the resonator to detect a change in the resonant frequency after being exposed to the particular gas and estimating the presence of the particular gas in the fluid downhole based on the change in the resonant frequency.

38. The apparatus of claim 37 wherein the membrane is one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

39. The apparatus of claim 37, wherein the resonator further comprises a sorbent for coating the resonator to detect the presence of one of: (i) CO2, and (ii) H2S.

40. The apparatus of claim 37, further comprising charcoal in the gas analysis chamber for adsorbing gases from the gas analysis chamber to prevent the gases from lingering in the gas analysis chamber.

41. A system for monitoring the presence of a gas in a fluid downhole comprising:
(a) downhole tool;
(b) a membrane for diffusing the gas from the fluid downhole into a gas analysis chamber in the downhole tool, wherein the gas analysis chamber forms a vacuum chamber;
(c) a resonator for detecting the presence of the gas in the fluid downhole; and
(d) a processor for monitoring the resonant frequency of the resonator to detect a change in the resonant frequency after being exposed to the gas and detecting the presence of the gas based on the change in the resonant frequency.

42. The system of claim 41 wherein the membrane is one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

43. A system for monitoring the presence of a gas in a fluid downhole comprising:
(a) downhole tool;
(b) a membrane for diffusing the gas from the fluid downhole into a gas analysis chamber in the downhole tool, wherein the membrane is supported to withstand a pressure difference between a vacuum pressure in the chamber and a downhole pressure;
(c) a resonator for detecting the presence of the gas in the fluid downhole; and
(d) a processor for monitoring the resonant frequency of the resonator to detect a change in the resonant frequency after being exposed to the gas and detecting the presence of the gas based on the change in the resonant frequency.

44. The system of claim 43, wherein the membrane is one of: (i) a semi-permeable membrane; (ii) a semi-permeable membrane backed with a sintered metal; (iii) a semi-permeable membrane backed with a perforated backing plate; (iv) a gas selectable membrane, and (v) a membrane that only allows only one or more gases to diffuse from the fluid downhole.

* * * * *